(12) United States Patent
Durbin et al.

(10) Patent No.: US 6,592,371 B2
(45) Date of Patent: *Jul. 15, 2003

(54) METHOD AND SYSTEM FOR IMAGING AND MODELING A THREE DIMENSIONAL STRUCTURE

(76) Inventors: Duane Durbin, 7660 Norcanyon Way, San Diego, CA (US) 92126; Dennis Durbin, 711 Marsolan, Solana Beach, CA (US) 92075

(*) Notice: Subject to any disclaimer, the term of this patent is extended or adjusted under 35 U.S.C. 154(b) by 0 days.

This patent is subject to a terminal disclaimer.

(21) Appl. No.: 09/993,110

(22) Filed: Nov. 6, 2001

(65) Prior Publication Data

US 2002/0055082 A1 May 9, 2002

Related U.S. Application Data

(63) Continuation-in-part of application No. 09/696,065, filed on Oct. 25, 2000, now Pat. No. 6,364,660, and a continuation-in-part of application No. 09/726,834, filed on Nov. 30, 2000, now Pat. No. 6,386,867.

(51) Int. Cl.[7] .......................... G01B 11/24; A61B 5/103; A61C 3/00
(52) U.S. Cl. .......................... 433/214; 433/29
(58) Field of Search .......................... 433/29, 213, 214, 433/215

(56) References Cited

U.S. PATENT DOCUMENTS

| | | | |
|---|---|---|---|
| 3,861,044 A | 1/1975 | Swinson | |
| 4,324,546 A | 4/1982 | Heitlinger et al. | |
| 4,575,805 A | 3/1986 | Moermann et al. | |
| 4,611,288 A | 9/1986 | Duret et al. | |
| 4,935,635 A | 6/1990 | O'Harra | |
| 4,964,770 A | * 10/1990 | Steinbichler et al. | 433/223 |
| 5,115,307 A | 5/1992 | Cooper et al. | |
| 5,359,511 A | 10/1994 | Schroeder et al. | |
| 5,372,502 A | 12/1994 | Massen et al. | |
| 5,401,170 A | 3/1995 | Nonomura | |
| 5,440,383 A | 8/1995 | Bacchus et al. | |
| 5,545,039 A | 8/1996 | Mushabac | |
| 5,759,030 A | 6/1998 | Jung et al. | |
| 5,857,853 A | 1/1999 | van Nifterick et al. | |
| 6,050,821 A | 4/2000 | Klaassen et al. | |
| 6,126,445 A | 10/2000 | Willoughby | |
| 6,210,162 B1 | 4/2001 | Chishti et al. | |
| 6,227,850 B1 | 5/2001 | Chishti et al. | |
| 6,364,660 B1 * | 4/2002 | Durbin et al. | 433/29 |
| 6,386,867 B1 * | 5/2002 | Durbin et al. | 433/31 |

FOREIGN PATENT DOCUMENTS

| | | |
|---|---|---|
| DE | 40 34 007 A1 * | 4/1992 |
| WO | WO 98/48242 * | 10/1998 |

* cited by examiner

*Primary Examiner*—Ralph A. Lewis

(57) ABSTRACT

Systems and methods for generating a three-dimensional (3D) model of a structure include coating the structure with a luminescent substance to enhance the image quality, the luminescent substance having an excitation range; and capturing one or more images of the structure through at least one image aperture each having a frequency sensitivity, wherein the frequency sensitivity of each image aperture is maximized for the luminescent material emission range.

22 Claims, 9 Drawing Sheets

METHOD AND SYSTEM FOR IMAGING AND MODELING A THREE DIMENSIONAL STRUCTURE

This application is a continuation-in-part application of U.S. application Ser. No. 09/696,065, filed Oct. 25, 2000 now U.S. Pat. No. 6,364,660 B1 and U.S. application Ser. No. 09/726,834, filed Nov. 30, 2000, now U.S. Pat. No. 6,386,867 B1 the contents of which are hereby incorporated by reference.

1. Field of Invention

The present invention relates to intra-oral methods and apparatus for optically imaging a structure and creating representative 3D models from the images.

2. Background

Determination of the surface contour of objects by non-contact optical methods has become increasingly important in many applications. A basic measurement principle behind collecting range data for these optical methods is triangulation. Triangulation techniques are based on elementary geometry. Given a triangle with the baseline of the triangle composed of two optical centers and the vertex of the triangle the target, the range from the target to the optical centers can be determined based on the optical center separation and the angle from the optical centers to the target.

Triangulation methods can be divided into passive and active. Passive triangulation (also known as stereo analysis) utilizes ambient light and both optical centers are cameras. Active triangulation uses only a single camera and in place of the other camera uses a source of controlled illumination (also known as structured light). Stereo analysis while conceptually simple is not widely used because of the difficulty in obtaining correspondence between camera images. Objects with well-defined edges and corners, such as blocks, may be rather easy to obtain correspondence, but objects with smoothly varying surfaces, such as skin or tooth surfaces, with no easily identifiable points to key on, present a significant challenge for the stereo analysis approach.

To overcome the correspondence issue, active triangulation, or structured light, methods project known patterns of light onto an object to infer its shape. The simplest structured light pattern is just a spot, typically produced by a laser. The geometry of the setup enables the calculation of the position of the surface on which the light spot falls by simple trigonometry. Other patterns such as a stripe, or 2-dimensional patterns such as a grid of dots can be used to decrease the required time to capture the image surface.

The surface position resolution of structured lighting methods is a direct function of the fineness of the light pattern used. The accuracy of active triangulation methods depends on the ability to locate the "center" of the imaged pattern at each image capture step. A variety of real-world situations can cause systematic errors to be introduced that affect the ability to accurately determine the true imaged pattern "center". Curved surfaces, discontinuous surfaces, and surfaces of varying reflectance cause systematic distortions of the structured light pattern on the surface which can increase the uncertainty in measuring the position of the surface being scanned.

Additional measurement uncertainty is introduced if a laser is used as the light source to create the light pattern. Due to the coherence of laser light, reflections from the surface create a random interference pattern, known as laser speckle, throughout space and at the image sensor. The result is an imaged pattern with a noise component that affects the "center" determination, causing measurement errors even from a flat surface. The difficulty of determining the "center" of the pattern is further compounded if the surface that the pattern is projected upon is not opaque but translucent. This type of surface can result in the projected pattern "blooming" at the illuminated surface because of the diffusion of light throughout the object. A tooth is an example of a translucent object that represents a challenging task from which to obtain a surface contour with active triangulation.

The dental and orthodontic field is one exemplary application for digitally generating 3D models of structures. In many dental applications, a working model of a patient's teeth is needed that faithfully reproduces the patient's teeth and other dental structures, including the jaw structure. Conventionally, a three-dimensional negative model of the teeth and other dental structures is created during an impression-taking session where one or more U-shaped trays are filled with a dental impression material. Impression materials include, among others, compositions based on alginates, polysulphides, silicones and vulcanizable polyether materials. The impression material is typically prepared by mixing a base component and a hardener or initiator or catalyst component. The impression tray containing the impression material, in its plastic state, is introduced into the mouth of the patient. To ensure a complete impression, an excessive amount of impression material is typically used. While the tray and impression material is held in place, the material cures, and after curing, the tray and material are removed from the mouth as a unit. The impression material is allowed to solidify and form an elastic composition, which is the negative mold after removal. The working model is obtained by filling this impression with a modeling material.

Dental patients typically experience discomfort when the dentist takes an impression of the patient's teeth. The procedure can be even more uncomfortable for the patient if the impression materials run, slump or are otherwise expelled into the patient's throat. Such situations can potentially cause a gag reflex reaction from the patient. In addition to patient discomfort, the impression process is time consuming. Additionally, the impression process can be error-prone. For example, when the impression material is not properly applied, the resulting working model may not accurately reflect features on the teeth. Moreover, the model can show air bubbles trapped during the impression taking session. Depending on the accuracy required, such working model may not be usable and additional dental impressions may need to be taken. Further, the mold and working model are fragile and can be easily damaged. The need to store the fragile models for future reference tends to become a logistical problem for a dental practice as the number of archived models accumulates.

Automated scanning techniques have been developed as alternatives to the mold casting procedure. Because these techniques can create a digital representation of the teeth, they provide the advantage of creating an "impression" that is immediately transmittable from the patient to a dental laboratory. The digital transmission potentially diminishes inconvenience for the patient and eliminates the risk of damage to the mold. For example, U.S. Pat. No. 6,050,821 discloses a method and apparatus for intraorally mapping the structure and topography of dental formations such as peridontium and teeth, both intact and prepared, for diagnosis and dental prosthetics and bridgework by using an ultrasonic scanning technique. As claimed therein, the method can provide details of orally situated dental formations thus enabling diagnosis and the preparation of precision moldings and fabrications that will provide greater comfort and longer wear to the dental patient. Also, as discussed therein, infra-red CAD/CAM techniques have been used to map impressions of oral structures and make single-tooth prosthetics.

Also, in certain applications such as restorative dentistry that is preformed on visible teeth, such as incisors, aesthetic considerations require that the prosthetic interface with the original tooth surface be underneath the gum (sub gingival) to eliminate the sight of the "joining line". In preparation for the prosthetic, the patient's tooth must be shaped to create a ledge or margin beneath the gum line where the prosthetic will be sealed to the existing tooth. To prepare this surface, the dentist typically places a retraction cord between the tooth and gum. The retraction cord creates a working space that allows the dentist to machine the margin around the tooth of interest.

In order for the finished prosthetic to be correctly sized and properly seated on the prepared tooth, it is essential that the impression of the prepared tooth contain an accurate representation of the sub gingival margin. Improper resolution of the margin in the impression and the subsequent creation of the prosthetic from this impression can result in a poor seal along the margin of the prepared tooth and the prosthetic. A poor seal along the margin has the potential to expose the underlying tooth to decay and the subsequent loss of the tooth—the very thing the prosthetic was suppose to prevent. Two methods are commonly used to accurately capture the margin during the impression process. The first method uses a retraction cord to hold the gum away from the tooth surface to allow the impression compound to flow underneath into the sub gingival region. The second method uses an impression material with low viscosity that under pressure is forced underneath the gums and thus captures the sub gingival margin.

In addition to obtaining sub gingival access for the impression material, the area of interest should be dry and clean (dry field) to obtain an accurate impression. A dry field is needed because typical impression compounds are hydrophobic and the presence of moisture when using a hydrophobic impression compound results in bubbles in the impression. The dry field is typically created by the dentist directing pressurized air across the prepared surface just prior to placing the impression tray in the patient's mouth.

From a surface imaging perspective, human teeth consist of two primary components: enamel and dentin. The bulk of the tooth consists of semi-transparent dentin that is covered by a thin translucent layer of enamel that consists almost entirely of calcium salts in the form of large apatite crystals. These micro crystals form prisms or rods with 4–6 $\mu$m transverse dimensions oriented normally to the tooth surface. The main dentin structural component is micrometer sized dentinal tubes, which radiate with an S-shaped curve from the pulp cavity toward the periphery. The crystalline nature of the enamel surface results in an optically anisotropic medium that results in double refraction or birefringence of the incident light pattern. Further, the translucent nature of the enamel results in a spreading or blooming of the incident structured light pattern as observed at the image sensor. Similar to the enamel, dentin also exhibits birefringence as well as having the dentinal tubes act as light pipes—further contributing to blooming. The observed color of a person's tooth is primarily the result of the frequency selective absorption and reflection of the dentin material.

To minimize the effects of the optical properties of teeth during imaging, several commercial systems (Sirona Inc. Cerac System and Orametrix Inc. Suresmile System) have the user apply a coating to the area that is to be imaged to create an opaque surface. Typically, titanium dioxide is used because of its' high index of refraction. Titanium dioxide is a white pigment that is commercially available in one of two crystalline forms: anatase or rutile and is widely used for providing brightness, whiteness, and opacity to such products as paints and coatings, plastics, paper, inks, fibers and food and cosmetics.

To achieve its' optical properties, titanium dioxide particles must be created with an ideal particle size of 0.3–1 $\mu$m. In powder form, titanium dioxide must be applied to a thickness of between 40 to 60 particles to achieve opacity on the tooth surface. This introduces an error into the true surface contour of the tooth that can vary from 12 $\mu$m to 60 $\mu$m. Since many dental procedures require surface accuracies of 25–50 $\mu$m the use of titanium dioxide imposes severe and unrealistic constraints on the error budgets of the remaining parameters involved with making an accurate measurement of the teeth surface contours. Further, because titanium dioxide is a crystalline material, it exhibits optical anisotropy so it is important that the applied thickness be sufficient to create a truly opaque surface to eliminate birefringence effects. In addition, because titanium dioxide is an optically rough surface, it provides no reduction in speckle noise if coherent light is used for the illumination source.

SUMMARY

Systems and methods for generating a three-dimensional (3D) model of a structure include coating the structure with a luminescent substance to enhance the image quality, the luminescent substance having an excitation range; and capturing one or more images of the structure through at least one image aperture each having a frequency sensitivity, wherein the frequency sensitivity of each image aperture is maximized for the luminescent material emission range.

For accurately determining the surface contour of a non-opaque object, the system provides a luminescent coating be applied to the surface of the object and then illuminated with a structured light pattern at a wavelength, $\lambda 1$, which corresponds to the excitation maxima of the luminescent compound. The incident light at $\lambda 1$ induces the luminescent compound to emit isotropic radiation at $\lambda 2$. The luminescent emission will only occur where the light pattern is incident on the surface. An optical filter is used to restrict the input to the image sensor to a narrow region around the luminescent compound's emission wavelength, $\lambda 2$, and filters out the incident pattern light at $\lambda 1$.

Advantages of the system may include one or more of the following. The system minimizes pattern blooming effect—when a light pattern is projected onto a translucent object both diffuse reflection and diffuse transmission occur. The effect of the diffuse transmission is to spread the pattern light in all directions within the object. Since translucent objects typically will a have relatively low reflection coefficient (<5%) the reflected surface pattern image intensity as seen by the image sensor will not be significantly larger than the diffuse transmitted light within the object—a phenomena which has the effect of making the pattern appear larger. Conversely, using a luminescent coating results in an unattenuated signal directly from the surface and "noise signals" that are reduced >95% by the reflection coefficient of the object.

The system also eliminates speckle noise—due to the independent nature of the excitation and emission processes of luminescence, the emitted photons are incoherent and thus do not constructively/destructively interfere in an ordered manner. The system works with luminescence compounds with small molecular size to minimize coating errors—luminescent compounds are available which allow hundreds of layers of material to be used yet still maintain sub-micron coating depths on the surface being measured. Moreover, the frequency shift of emitted luminescent light away from the incident pattern illumination frequency allows greater image sensor sensitivity and reduces the dynamic range requirements.

The system also provides a spray orifice to coat dental structure with substance to improve the imaging capability. Images of the dental structures are captured with sufficient resolution such that the acquired images can be processed into accurate 3D models of the imaged dental structures. The images and models would have application in dental diagnosis and for the specification and manufacture of dental working models, dental study models and dental prosthetics such as bridgeworks, crowns or other precision moldings and fabrications.

Further, the system provides automated intra-oral scanning of all the dental structures in the jaw through an optical aperture and combines the information available in the entire set of images to create and present an accurate 3D model of the scanned structures. The system allows intra-oral images of dental structures to be taken rapidly and with high resolution such that the acquired images can be processed into accurate 3D models of the imaged dental structures. The images and models can be used in dental diagnosis and used for the specification and manufacture of dental prosthetics such as bridgeworks, crowns or other precision moldings and fabrications. In addition, the system produces 3D models useful in the diagnosis and treatment planning process for dental malocclusions. The system-produced data representing a set of dental images and models can be transmitted electronically to support activity such as professional consultations or insurance provider reviews, and the images and models may be electronically archived for future reference.

The digital 3D model of patient's teeth and other dental structures has advantages over a conventional cast physical model due to the following: 1) 3D model efficiently created in a single step with accuracy meeting or exceeding the conventional multiple step impression technique; 2) reduced storage costs; 3) immediate, labor-free retrieval and archiving; 4) no model breakage; 5) integrates directly into computer based analysis tools for diagnosis and treatment planning; 6) digital models backup; 7) e-mails to colleagues, dental specialists, insurance companies; 8) access to information from home, satellite office; 9) effective presentation tool; 10) no mess and dust; and 11) no wasted staff time.

The above and other features and advantages of the present invention will be apparent in the following detailed description of the preferred embodiments of the present invention when read in conjunction with the accompanying drawings in which corresponding parts are identified by the same reference symbol.

Description

Figure 1:
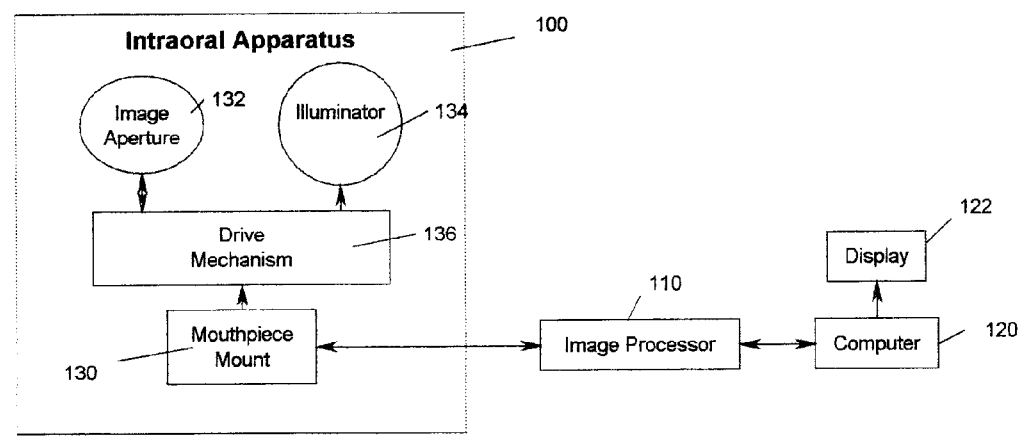
FIG. 1 illustrates an embodiment of a system for performing intra-oral scanning and for generating 3D models of teeth and other dental structures.

Referring to FIG. 1, a system block diagram depicting the instrumentation used in scanning teeth and other dental structure images and in generating 3D models, will facilitate a general understanding and appreciation of the disclosed method and apparatus.

In FIG. 1, an intra-oral scanner 100 is adapted to be placed inside the mouth of the patient (intra-oral cavity). The intra-oral scanner 100 captures images of various dental structures in the mouth and communicates this information with a remote image processor 110. The remote image processor 110 in turn can communicate with a computer 120 and can display images of the dental structures on a display 122 connected to the computer 120. Alternatively, functionalities of the computer 120 such as data storage and display can be provided directly by the remote image processor 110 in another embodiment. Images and 3D models derived from the images can be transmitted as digital files to other equipment or locations by the computer 120.

In one implementation, the intra-oral scanner 100 is embedded in an intra-oral structure, such as a mouthpiece 130. An image aperture 132 is provided to capture images of the dental structures. The image aperture 132 can be an objective lens followed by relay lens in the form of a light-transmission cable such as a fiber optic cable to transmit images of the dental structures along a pre-selected distance to a camera. The fiber optic cable transmits light through small filamentary optical materials or fibers. Typically, the fibers include a central core and an outer surrounding cladding along the entire length of the fiber. The transmission of light through the fiber is based on the phenomenon of total internal reflection. For total internal reflection, the refractive index of the core is greater than the refractive index of the cladding. In one embodiment, optical fibers for the transmission of images comprised of visible through mid-infrared light can be used.

The output of the image aperture 132 can be provided to one or more sensors for detecting and converting incident light (photons from the light source reflected off the dental structure surface)—first into electronic charge (electrons) and, ultimately into digital bits. In one implementation, the output of the image aperture 132 is provided to a camera (not shown), which can be analog or digital. In one embodiment, the camera contains one or more image sensor(s) used to create digital images of the dental structure. These sensors can be devices such as a charge-coupled device (CCD) sensor or a complementary metal oxide semiconductor (CMOS) image sensor. The image sensor can be an array of individual photosensitive cells (pixels) whose size determines the limiting resolution. Image sensor arrays can have from 16×16 pixels to more than 1024×1024 pixels, and the arrays can be symmetrical or asymmetrical.

Further, a source of light delivered through an illuminator 134 is provided to illuminate the dental structures to improve the quality or contrast of the images taken by the image aperture 132. The light can be white light, light shown in one or more colors, or can come from a laser beam. The intensity of the light source used to illuminate the dental structure is ideally controllable and is in the frequency range of visible or infra-red light. In one embodiment, the light source can be integral to the mouthpiece 130. In another embodiment, light can be routed from the light source to the illuminator 134 by one or more fiber optic cables (not shown). This bundle of optical fibers can be positioned to surround the outer circumference of the image aperture 132 to create a plurality of illuminators. The field of illumination may be greater than the field of view of the image aperture 132 and may range up to 180 degrees. In another embodiment, the field of illumination may be a focused beam that illuminates a spot on the dental structure with an illumination spot size of dimensions less than 5 mm.

A drive mechanism 136 is provided to incrementally or continuously move the image aperture 132 and the illuminator 134 to various positions in the intra-oral cavity. In one embodiment, the image aperture 132 and the illuminator 134 are movably mounted on a track that is driven by the drive mechanism 136. The track can be a U-shaped track conforming to the shape of the patient's arch. The drive mechanism 136 can be electrically actuated to move the image aperture 132 and the illuminator 134 around all teeth and other structures in the jaw. Any of a variety of drive motors can be used, and the power of the motor through the drive mechanism 136 can be translated into motion for the image aperture 132 and the illuminator 134 through rotary, linear, hydraulic, or pneumatic mechanisms for example.

Figure 2:
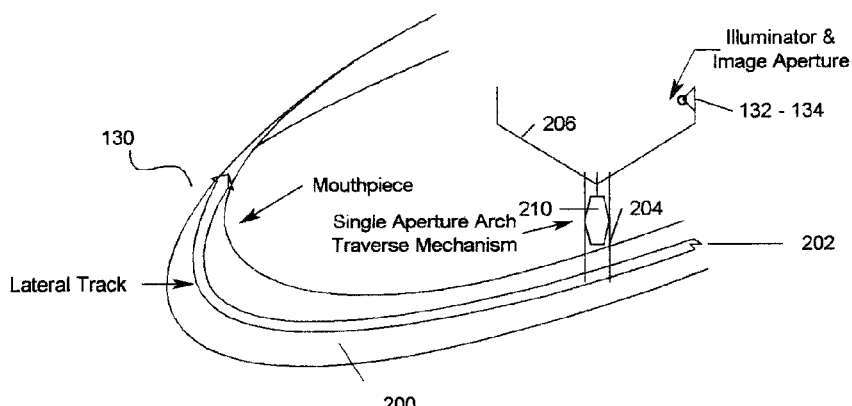
FIG. 2 shows an exemplary embodiment of a scanner with one aperture.

The intra-oral apparatus, as exemplified by mouthpiece 130, provides the mechanism for traversing image aperture 132 and the illuminator 134 around the oral cavity and positioning the image gathering aperture(s) 132A and illuminator(s) 134 at known positions while taking images of the dental structures. The mouthpiece 130 in one embodiment includes a sensor arc track 210 that allows the image aperture to traverse an arc to capture the image of the dental structure while also moving laterally (FIG. 2). In another embodiment, the mouthpiece 130 supports multiple image gathering apertures in known mechanical alignment and moving of said apertures laterally around the oral cavity (FIG. 3).

Although the scanning of one jaw arch at a time has been described, it is to be understood that two mouthpieces can be simultaneously deployed to capture images of dental structures on both the upper and lower jaw arches.

FIG. 2 shows one embodiment of the mouthpiece having a single image aperture. In the embodiment of FIG. 2, the mouthpiece 130 has a base 200 that is shaped substantially in an arch-shape or U-shape. Mounted on the base 200 is a lateral rail or track 202 that also conforms to the arch shape or U-shape. The track 202 supports a movable shuttle 204 driven by the drive mechanism 136. The shuttle 204 has an upwardly extending arm 206. Resting on top of the arm 206 are the image aperture 132 and the illuminator 134 of FIG. 1. Additionally, the arc track 210 allows the arm 206 to move from a frontal to a posterior view of the teeth. At each lateral position, the image aperture 132 traverses the arc track 210 over the dental structure to collect a sufficient number of images on both sides of the dental structure before moving to the next lateral position and repeating the process. The track 202 also includes sensors or indicators such as scale marks located at either end of the track 202 and along the track to provide image aperture positional feedback information. Alternatively, positional information can be ascertained by methods such as counting drive motor revolutions and deducing the position based on counting motor revolutions.

Figure 3:
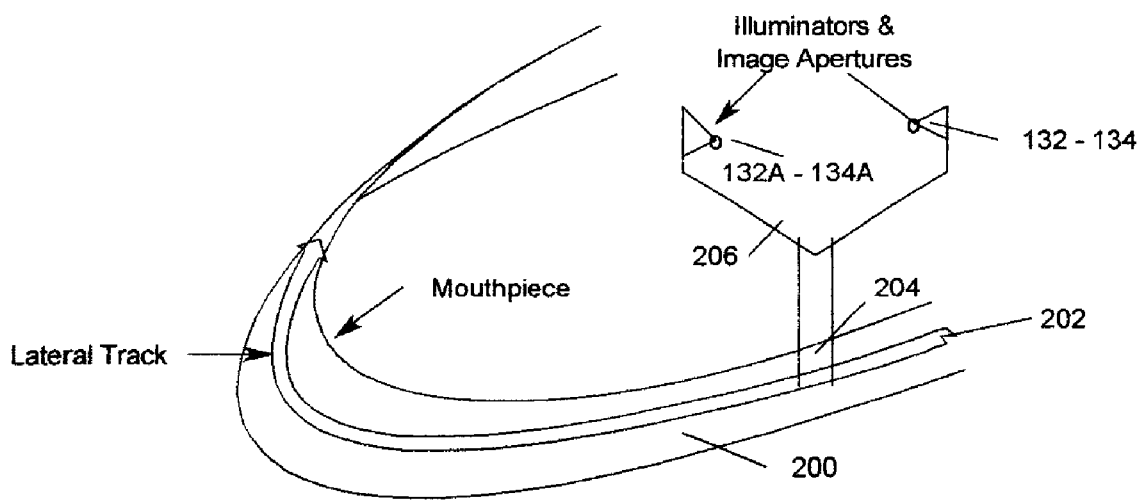
FIG. 3 shows a second embodiment of a scanner with a plurality of apertures.

FIG. 3 shows another embodiment with multiple image apertures that require only lateral motion. In this embodiment a plurality of image apertures 132A and the illuminator (s) 134A are mounted in a known orientation to one another on a laterally moveable apparatus. The number of image apertures and their orientation is selected to provide sufficient coverage and overlap of the dental structure to be modeled at the desired resolution. At each lateral position, an image from each of the apertures 132A is recorded for later processing. In either embodiment of FIG. 2 or FIG. 3, the image apertures 132 or 132A may be sensors integral to the mouthpiece or fiber optic image bundles connected directly to the mouthpiece. In the latter case, the fiber optic image bundle transmits the image to the image sensor on an external printed circuit board (PCB). To optimize the image collection at the image aperture, mirrored surfaces and optical lenses may be employed to direct and focus the image onto the image sensor.

As discussed above, the intra-oral scanner 100 contains components that support one or more of the following functions: 1) illuminate the dental structure to be imaged; 2) digitally image a dental structure from different aspects; and 3) reposition both the illumination and imaging apertures so as to traverse the entire intraoral cavity.

The intra-oral scanner 100 can be self-powered or power can be provided by the image processor 110. Further, the output of the intra-oral scanner 100 is received and processed by the image processor 110. In one embodiment, the output of the scanner 100 includes images transmitted through a fiber optic cable. These images are provided to a camera that digitizes the images and stores the digital images in a memory buffer. In a second embodiment, the output of the scanner 100 is already in digital form, and this data is stored in the memory buffer of the image processor 110 for processing, as described in more detail below.

Figure 4:
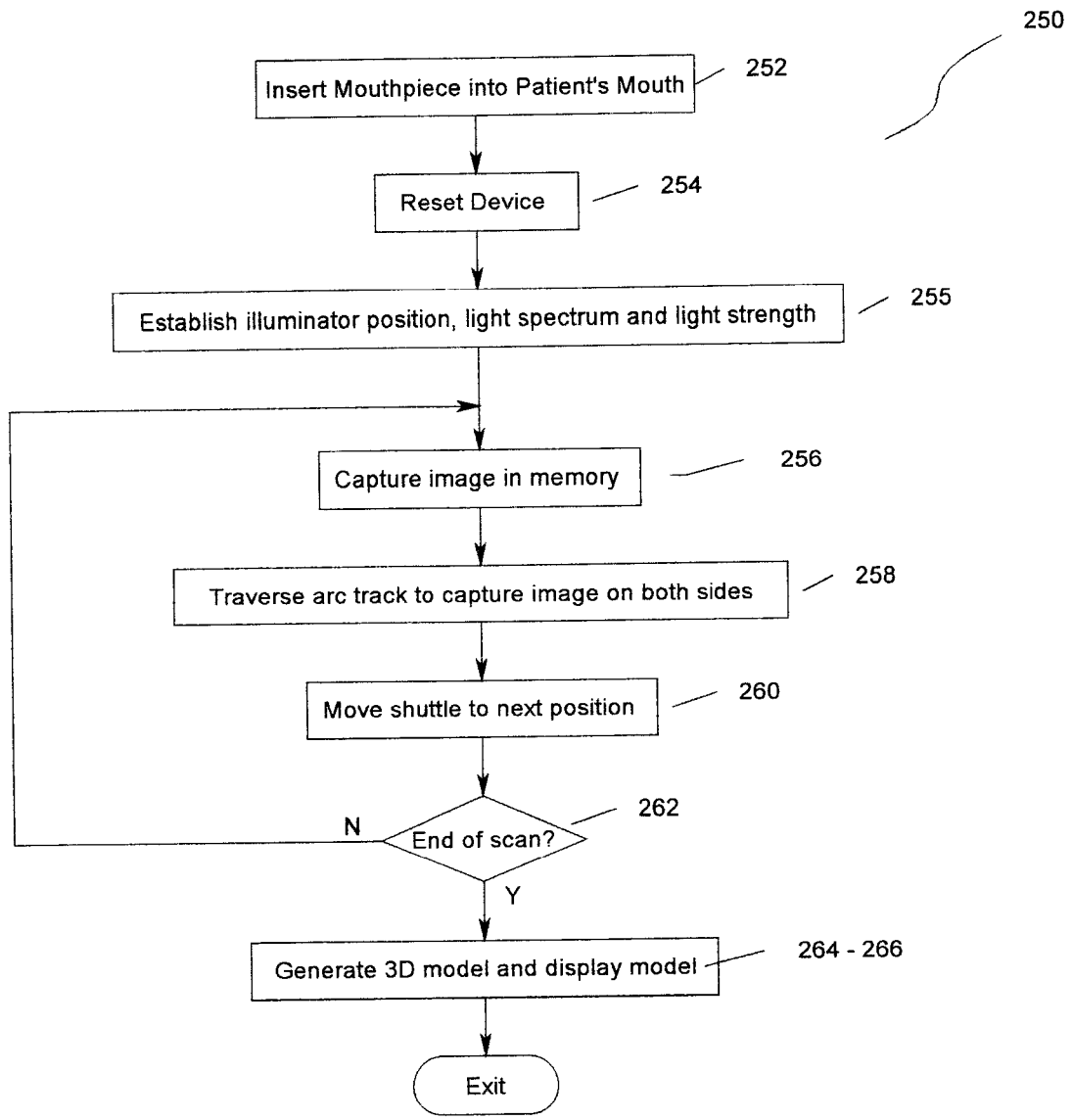
FIG. 4 illustrates a process in capturing images and generating 3D models from a patient.

FIG. 4 shows an exemplary process 250 for scanning and generating 3D models of dental structures. First, the mouthpiece 130 is inserted into the patient's mouth (step 252). Next, a reset operation is performed to move the shuttle 204 to an initial known position (step 254). The illuminator 134 position, light spectrum and light strength is established (step 255). The image processor 110 receives an image through the image aperture 132 and captures the image to its memory (step 256). The image processor 110 then instructs the image aperture 132 to traverse the arc track 210 over the dental structure to collect a sufficient number of images on both sides of the dental structure (step 258). The image processor 110 then actuates the drive mechanism 136 to move the shuttle 204 to the next incremental lateral position (step 260). At each lateral position, the image aperture 132 traverses the arc track 210 over the dental structure to collect a sufficient number of images on both sides of the dental structure before moving to the next lateral position. Next, the process 250 tests whether the shuttle 204 reaches the end of the patient's arch (step 262). If not, the process loops back to step 256 to continue the image acquisition operation. If the end has been reached, the process 250 generates a 3D model using the captured images (step 264) and displays the 3D model for review (step 266).

Figure 5:
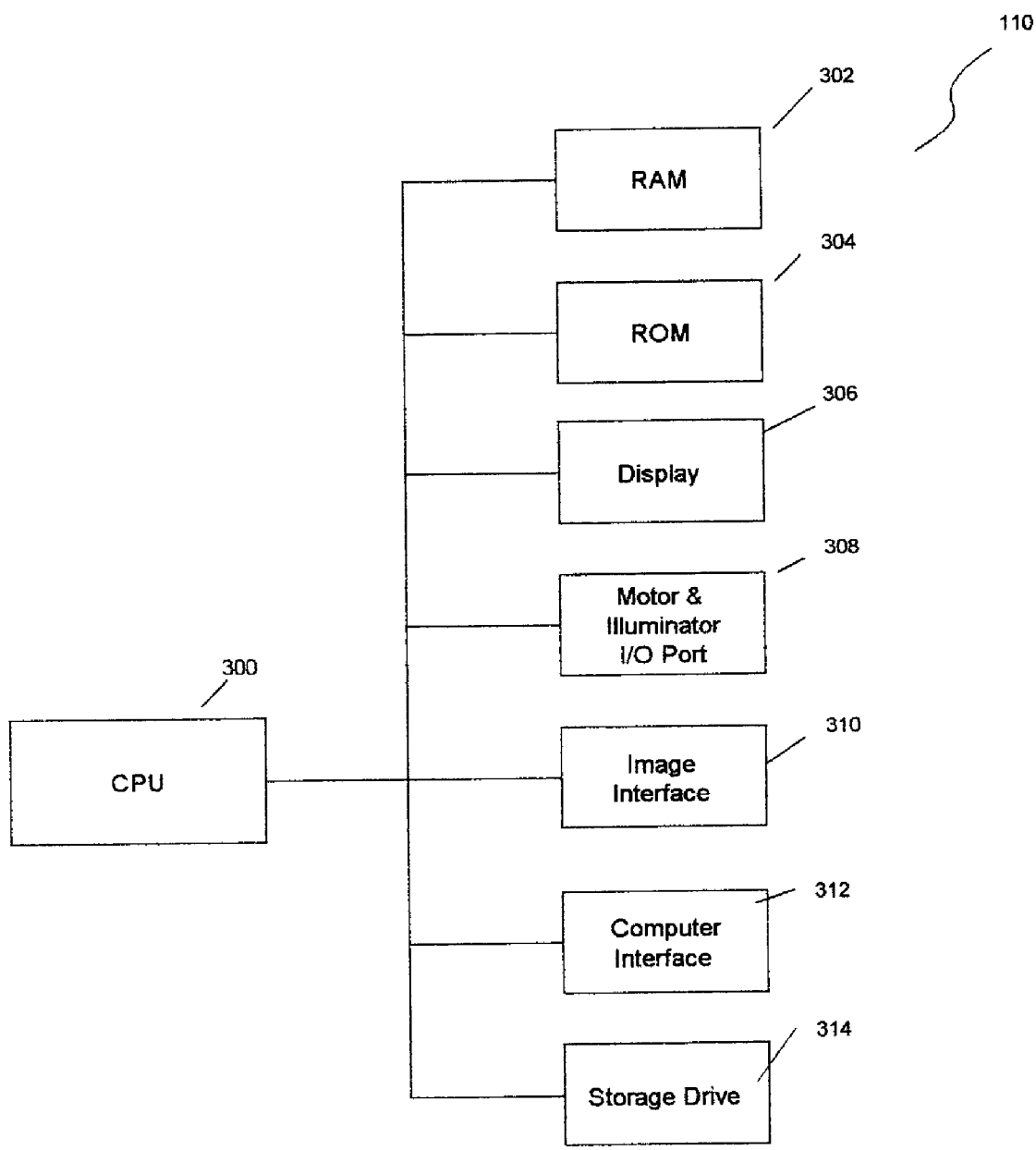
FIG. 5 shows an exemplary image processor for generating 3D models.

Turning now to FIG. 5, an exemplary image processor 110 is shown. The image processor 110 includes a central processing unit (CPU) 300, which can be a high performance CISC or RISC processor. The CPU 300 is connected to random access memory (RAM) 302 and read only memory (ROM) 304. The CPU 300 also is connected to a plurality of input/output devices, including a display 306, a motor and iluminator input/output port 308 to control the drive mechanism 136 and the illuminator 134 (FIG. 1), an image interface 310 to receive image data from the scanner 100, and a computer interface 312. The CPU 300 can also be connected to a storage drive 314 such as a hard drive to store software and data and provides an interface for the communication of data with other equipment.

The CPU 300 executes code to control the image data acquisition and generate 3D models from the captured images. The captured images are processed with a pattern recognizer that maps various points of an object observed in the captured images, thereby obtaining the shape/contour information. In one implementation, 2D digitized images of the dental structures are output from the scanner 100 and stored in computer memory of the image processor 110 along with the positional information and illuminator settings. The stored images from a plurality of images obtained at different positions of the image aperture are then analyzed using stereometric methods to form a 3D view. This process is repeated for the complete set of captured images to create a full 3D model of the scanned dental structures in the oral cavity. The 3D model is then presented on a display or used in conjunction with a CAD/CAM system for patient diagnosis and treatment.

Figure 6:
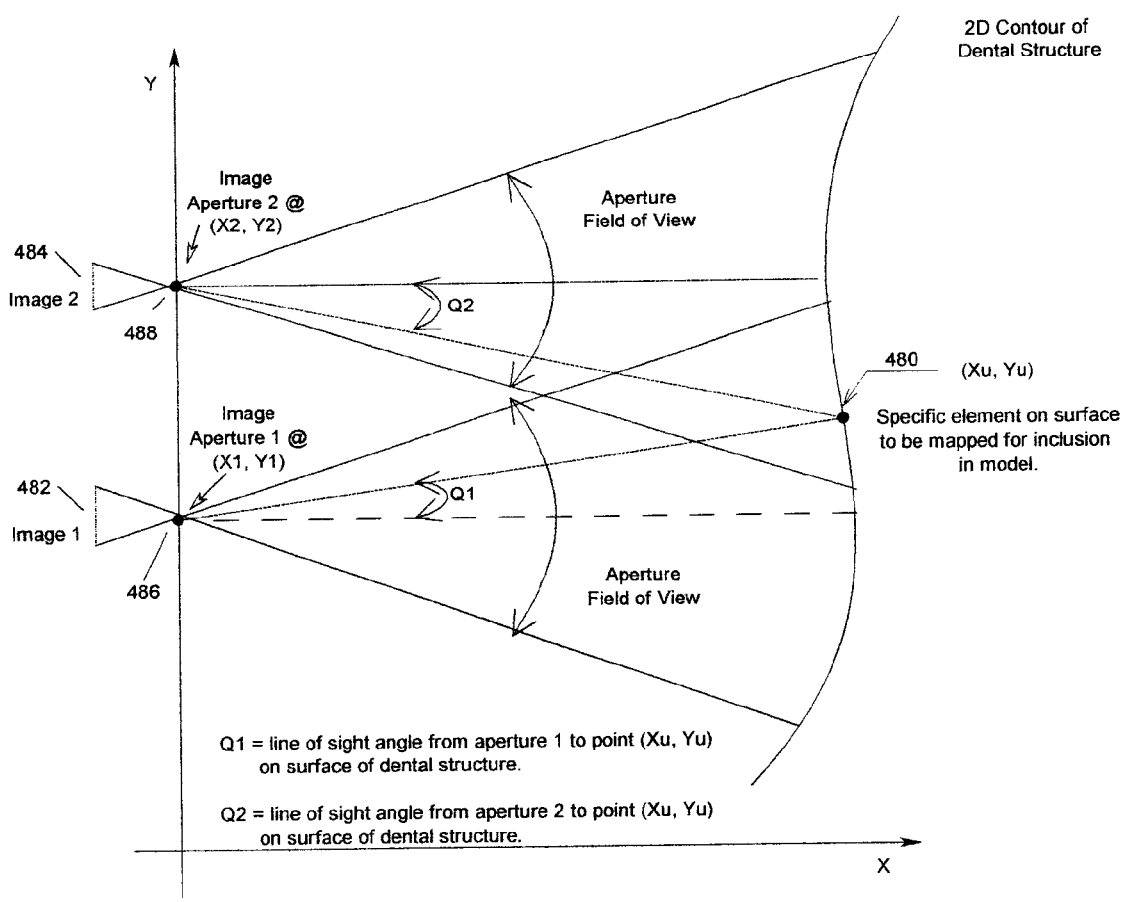
FIG. 6 shows an exemplary embodiment for modeling surface location and contour from stereo images.

FIG. 6 shows an exemplary embodiment for using stereo images to model the surface contour of dental structures. The example of FIG. 6 is described in terms of two-dimensions, but the process is readily extended to the third axis to derive three-dimensional surface contours for 3D models. With reference to FIG. 6, the following process is used to derive the position of a specific scene element 480 observed in images 482 and 484 captured through image apertures 486 and 488.

The image processor uses conventional image pattern matching techniques to identify a scene element that is observed in both image 482 and image 484. Further, based upon the image aperture field of view angle and the location of the specific scene element within the image sensor's array of pixels, the line of sight angle between the geometric plane of the image sensor and the scene element is derived. These line of sight angles are denoted in FIG. 6 as Q1 for an image aperture located at X1, Y1 and Q2 for an image aperture located at X2, Y2.

Let the as yet unknown coordinates for the location of the scene element of interest be denoted $x_u$ and $y_u$.

Based upon the geometry of the case of FIG. 6, $$y_u = (\tan Q1 \cdot x_u) + y_1$$

and $$\tan Q2 = (y_2 - y_u)/x_u$$

The value of $x_u$ and $y_u$ can now be solved using the above two equations and conventional techniques applicable to sets of linear equations. The stereometric method above can be generalized to add a third dimension $z_u$ and thereby derive a 3D surface contour or model of the imaged dental structure. The 3D version is based on differences in the line of sight angles projected into the third dimension to a dental structure element as viewed from at least two different aperture locations.

While for illustrative purposes this description is based upon the use of just two images, it is to be understood that the concept can be extended to more precisely find the 3D coordinates of a scene element by utilizing a multitude of images of the dental structure, taken from a multitude of image aperture positions and utilizing a multitude of illumination conditions.

In another implementation, image-processing operations based on triangulation can be used where beams of light are projected onto the dental structures and three-dimensional spatial locations are determined for points where the light reflects from the dental structure object. As the reflected light bounces off the object at an angle relative to the known location and bearing of the light source, the system collects the reflection information from a known location relative to the light source and then determines the coordinates of the point or points of reflection by triangulation. A single dot system projects a single beam of light which, when reflected, produces a single dot of reflection. A scan line system beams a plane of light against the dental structure and which is reflected as a curvilinear-shaped set of points describing one contour line of the object. The location of each point in that curvilinear set of points can be determined by triangulation. The system projects a light plane (i.e., a laser stripe) from a known location and reads the reflection of multiple points depicting the contour of the dental structure at a location distant from the camera and from which the position can be triangulated.

In addition to optical triangulation systems, other alternative optical scanning systems can be used, including range meters systems. Range meter systems typically use an infrared-pulsed laser and mechanical scanning techniques to project a dot laser across an object and then measure the phase delay of the reflected signal.

Once the dental structure coordinates have been scanned, the system removes redundant points and generates a 3D model from the scanned data using various techniques known in the art. In one embodiment, the process examines data for two adjacent laser stripes. Next, the process sweeps through each Y coordinate from the top of the two laser stripes to the bottom of the two stripes and creates triangles for the geometric 3D model. When the process has reached the bottom of the stripes, the triangulating process for the current laser stripes is finished and the next set of adjacent scan lines are retrieved until a triangulated mesh covering the whole dental structure is generated. Once the mesh has been generated, a 3D model with realistic shading and lighting can be generated.

Figure 7:
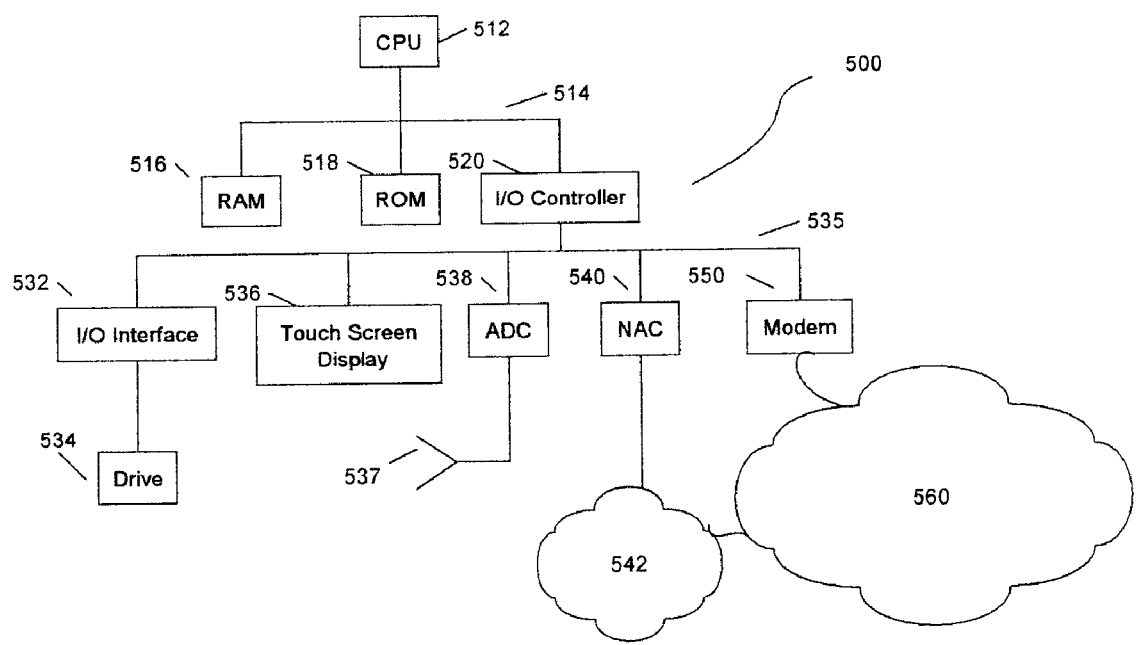
FIG. 7 shows an exemplary computer for using the 3D models.

FIG. 7 shows an exemplary computer 500 for processing dental image data and for generating 3D models. The system 500 includes a processor (CPU) 512, RAM 516, ROM 518 and an I/O controller 520 coupled by a CPU bus 514. The I/O controller 520 is also coupled to an I/O bus 535. The I/O bus 535 communicates with an I/O interface 532 that in turn controls a solid state drive (flash RAM) 534 or a removable disk drive. The I/O bus 535 is also connected to input devices such as a touch-screen display 536. In place of, or in parallel with the touch-screen display 536, a keypad can be connected to the I/O bus 535 to receive user data entry. Alternatively, voice recognition can be used in conjunction with and/or replace the touch-screen display 536 or keypad. In such an embodiment, a microphone 537 is connected to an analog to digital converter (ADC) 538 that interfaces with the processor 512.

A network access card 540 can be connected to the I/O bus 535 to allow the computer 500 access to a network 542.

Through the network 542, or through a modem 550 connected to the I/O bus 535, the computer 500 can access a wide area network 560 such as the Internet. An Internet community with one or more service providers or marketers is connected to the network. The Internet community can provide value added services such as services to create a physical teeth model from the 3D model.

Figure 8:
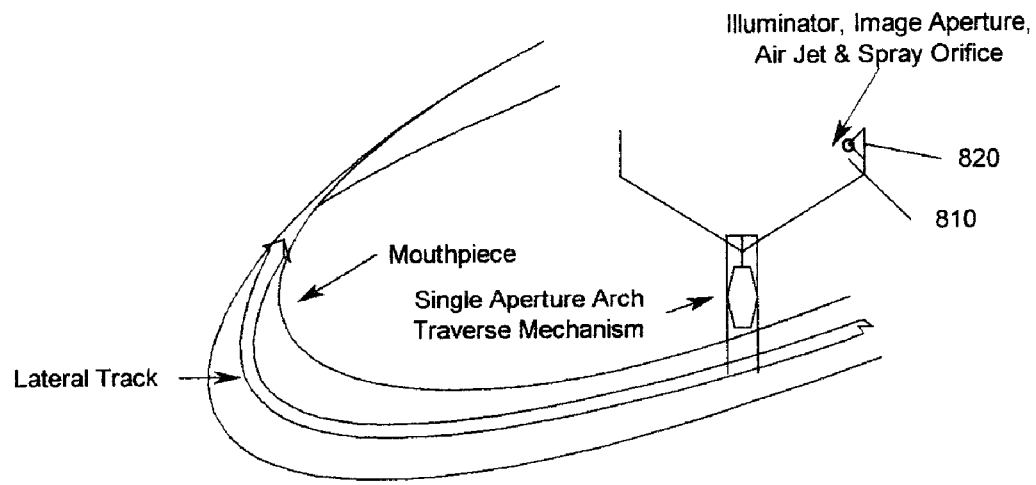
FIG. 8 shows a third exemplary embodiment of a scanner with one aperture, air nozzle and spray orifice.
Figure 9:
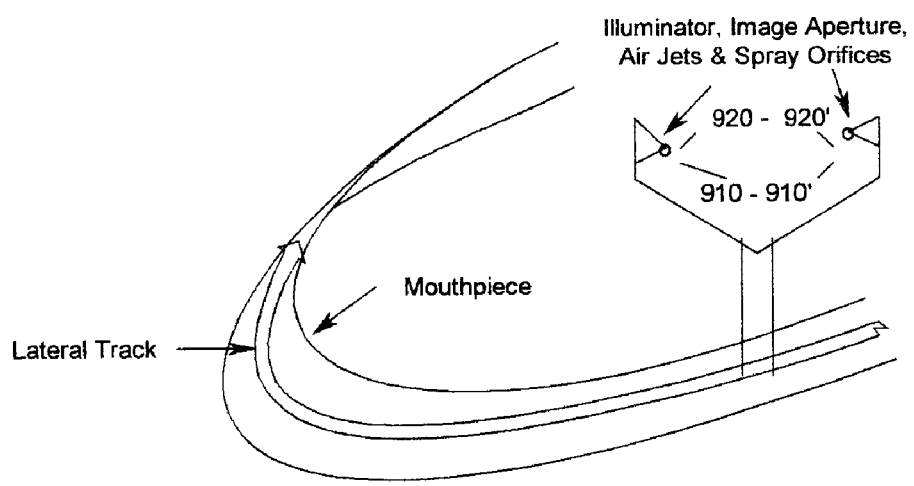
FIG. 9 shows a fourth embodiment of a scanner with a plurality of apertures, air nozzles and spray orifices.

FIGS. 8–9 shows additional embodiments providing additional capabilities of directing pressurized air at the dental structure that is being imaged to 1) create a dry field; and 2) allow sub gingival image capture. Furthermore, these embodiments provide a spray orifice for dispensing a coating substance such as titanium dioxide or a luminescent compound onto the dental structures during the digital imaging process. The timing, duration and intensity of the directed air source and spray dispensing on the dental structure are precisely controllable. In one implementation, the pressurized air source is obtained by interfacing the apparatus to an existing air source using an industry standard interface at the patient dental chair.

One embodiment of the mouthpiece uses a single air jet 810 and spray orifice 820 (FIG. 8). At each lateral position, as the image aperture traverses an arc over the dental structure, the air jet output is directed at the region of the dental structure currently being imaged and is synchronized with the image capture. The spray orifice is also directed at the dental structure being imaged but dispenses the coating prior to image capture.

Yet another embodiment uses multiple air jets to simultaneously direct air at multiple regions of the dental structure in synchronism with the capture of the dental structure images (FIG. 9). In this embodiment a plurality of air jets 910 and 910' are mounted in a known orientation to one another on a laterally moveable apparatus. The number of air jets and their orientation is selected to provide sufficient coverage and overlap of the dental structure to be digitally imaged and modeled. In the embodiment of FIG. 9, multiple spray orifices 920 and 920' are integrated into the mouthpiece to provide coverage of all areas that are being imaged. In either embodiment (FIG. 8 or 9), the pressurized air source may be integral to the mouthpiece or connected directly to the mouthpiece via tubing. In the latter case, the pressurized air source is ideally an existing source located at the patient dental chair. The mouthpiece would connect to this source using a standard industry interface.

In one embodiment, the air nozzle receives air from an air source through a flexible hose such as a rubber hose. The air supply is passed through an air regulator that is in turn connected to an air solenoid to turn on and off the air at appropriate time.

A stream of air is directed at the surface of the dental structure using the nozzle. As the air is directed in a thin low pressure stream onto the dental structure, the particles may be dislodged from the surface of the dental structure while the dental structure is dried. The air flow or stream is preferably directed at the dental structure in a substantially fan-shaped or conical flow pattern so that air strikes the structure at a range of angles up to about 45 degrees with respect to the surface of the tooth. This conical flow pattern is elliptical in cross-section with a length as much as two to three times its width.

In another embodiment for spraying materials such as whitening ingredients or a luminescent compound to the dental structure, air supplied by a compressor is delivered to a chamber in the nozzle. The compressed air in the chamber creates suction on a material line, which runs from the chamber to a tank containing the coating material. The suction draws material from the tank into the chamber and entrains the material with the compressed air for delivery onto the dental structure.

Figure 10:
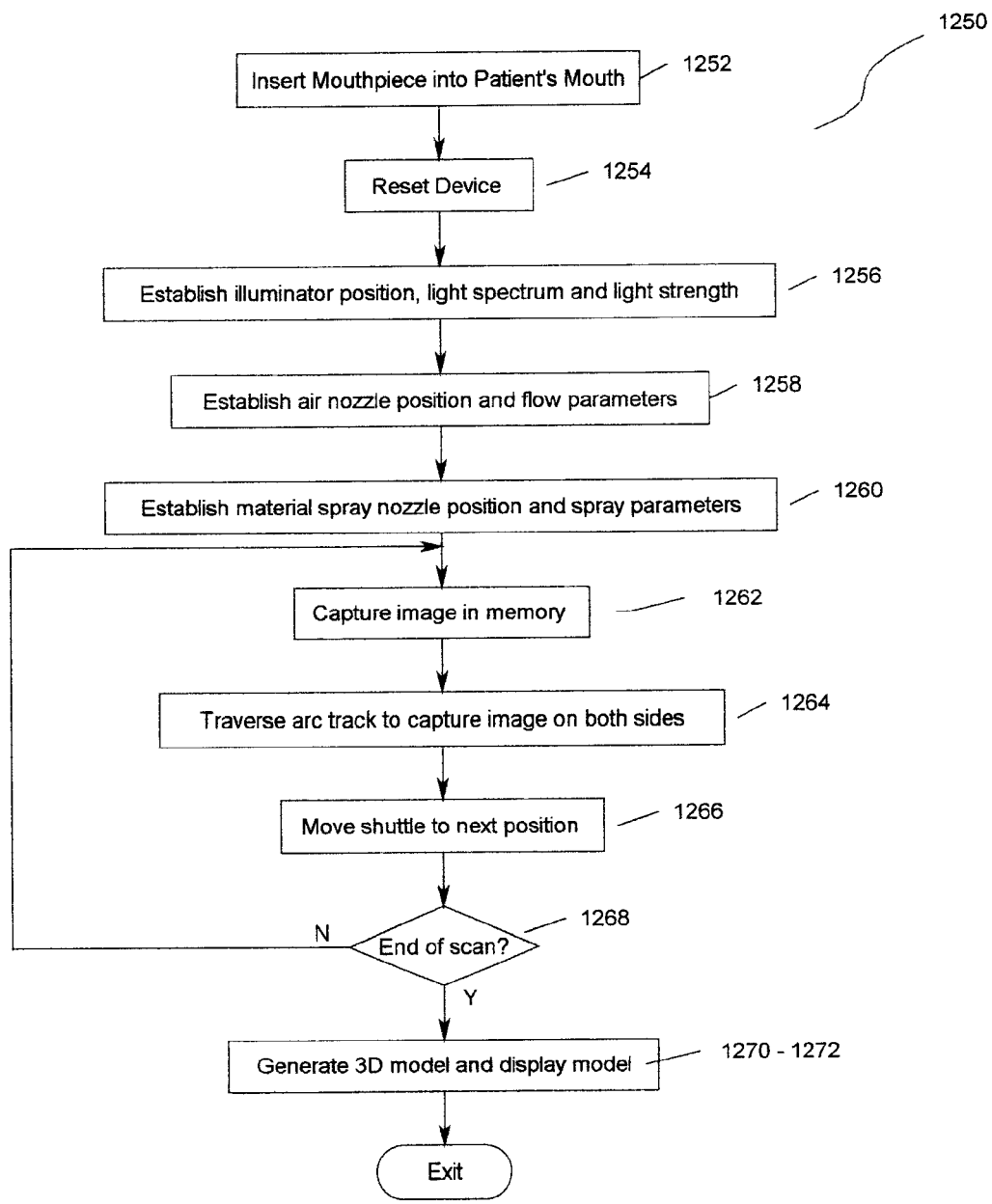
FIG. 10 illustrates a process utilizing air jets and spray orifices while capturing images and generating 3D models from a patient.

FIG. 10 shows an exemplary process 1250 utilizing an air nozzle and spray nozzle for scanning and generating 3D models of dental structures. First, the mouthpiece 130 is inserted into the patient's mouth (step 1252). Next, a reset operation is performed to move the shuttle 204 to an initial known position (step 1254). The illuminator 134 position, light spectrum and light strength are established (step 1256). The air nozzle 810 position and air flow characteristic are established (step 1258). The coating material spray nozzle 820 position and spray parameters are established (step 1260). The image processor 110 receives an image through the image aperture 132 and captures the image to its memory (step 1262). The image processor 110 then instructs the image aperture 132 to traverse the arc track 210 over the dental structure to collect a sufficient number of images on both sides of the dental structure (step 1264). The image processor 110 then actuates the drive mechanism 136 to move the shuttle 204 to the next incremental lateral position (step 1266). At each lateral position, the image aperture 132 traverses the arc track 210 over the dental structure to collect a sufficient number of images on both sides of the dental structure before moving to the next lateral position. Next, the process 1250 tests whether the shuttle 204 reaches the end of the patient's arch (step 1268). If not, the process loops back to step 1262 to continue the image acquisition operation. If the end has been reached, the process 1250 generates a 3D model using the captured images (step 1270) and displays the 3D model for review (step 1272).

Figure 11:
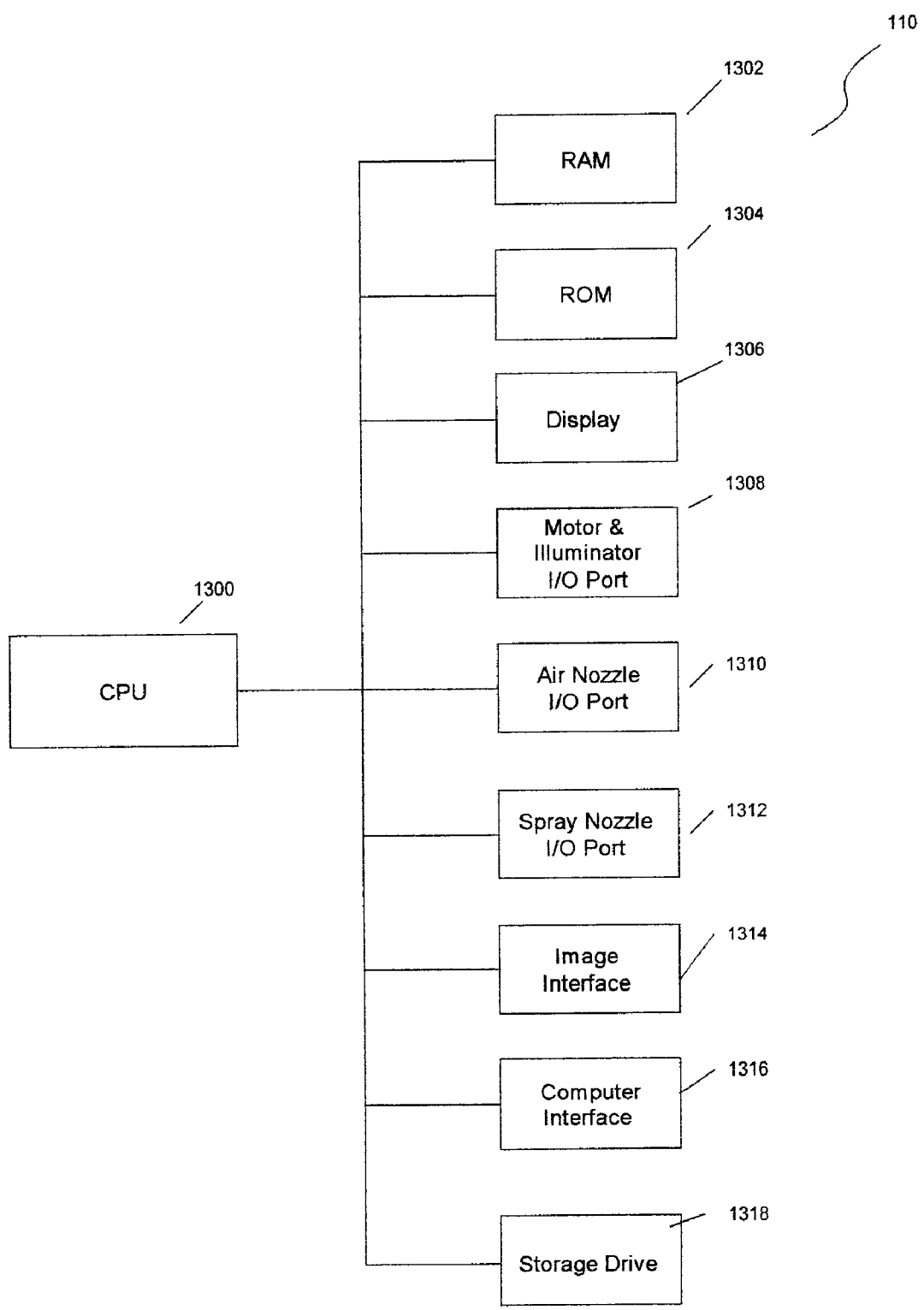
FIG. 11 shows an exemplary image processor for generating 3D models with controls for air jets and spray orifices.

Turning now to FIG. 11, an embodiment of an image processor 110 that includes control of an air nozzle and spray nozzle is shown. The image processor 110 includes a central processing unit (CPU) 1300, which can be a high performance CISC or RISC processor. The CPU 1300 is connected to random access memory (RAM) 1302 and read only memory (ROM) 1304. The CPU 1300 also is connected to a plurality of input/output devices, including a display 1306, a motor and illuminator input/output port 1308 to control the drive mechanism 136 and the illuminator 134 (FIG. 1), an air nozzle I/O port 1310 to control the position and operation of the air nozzle 810 (FIG. 8), a spray nozzle I/O port 1312 to control the position and operation of the material spray nozzle 820 (FIG. 8), an image interface 1314 to receive image data from the scanner 100, and a computer interface 1316. The CPU 1300 can also be connected to a storage drive 1318 such as a hard drive to store software and data and provides an interface for the communication of data with other equipment.

The above system supports a rapid imaging of dental structures in such a way, and with sufficient resolution such that the acquired images can be processed into accurate 3D models of the imaged dental structures. The images and models can be processed on the computer 500 to provide dental diagnosis and to support the specification and manufacture of dental prosthetics such as bridgeworks, crowns or other precision moldings and fabrications. The computer 500 can transmit data representing a set of dental images and models over a wide area network such as the Internet to support activity such as professional consults or insurance provider reviews and the images and models may be electronically archived for future reference.

Next, a method for generating a three-dimensional model of a non-opaque structure, is discussed. The structure can be a large object such as a car or a small object such as teeth, among others. The method includes coating the structure with a luminescent substance to enhance the image quality, the luminescent substance having an excitation range; operating an illumination source at a frequency within the excitation range of the luminescent material; and capturing one or more images of the structure through at least one image aperture each having a frequency sensitivity, wherein the frequency sensitivity of each image aperture is maximized for the luminescent material emission range.

Luminescence substances, compounds or materials are defined as those that when a molecule of which has absorbed a quantum of radiation (a photon) and has thereby been raised to an excited energy state, relaxes back to the lower energy state it emits a photon, typically at a lower frequency then the exciting radiation. Luminescent compounds have been used in a variety of commercial and medical applications including diagnostic assays, toothpaste and light bulbs. In addition, use has been made of the naturally occurring or auto-luminescence of objects. One such example is determination of dental caries using changes in the auto-fluorescence of a tooth by a technique known as quantitative light fluorescence.

There are two basic emission processes: fluorescence and phosphorescence. Fluorescence is the process of fast emission—typically occurring about $10^{-8}$ seconds after the excitation absorption. Phosphorescence is a slower and less common process that occurs $10^{-5}$ to 10 seconds after excitation. Fluorescence involves two independent processes, absorption and emission and thus has both an excitation and emission spectrum. Because these are independent processes at the molecular level, the emitted light from a luminescent compound is not coherent. The emitted spectrum typically appears at longer wavelengths (lower energy) because of the energy lost in the excited state by non-radiative vibrational relaxation. The wavelength separation between the excitation and emission spectrums is called the Stokes shift and varies from as little as a few nanometers (nm) to greater than 150 nm depending upon the particular fluorescent compound. In addition, the molecular weight of fluorescent compounds varies from several hundred daltons to millions of daltons (one dalton is $\frac{1}{12}$ of the mass of carbon 12). The diameter of fluorescent compounds is directly related to their molecular weight and varies from tenths of an angstrom to thousands of angstroms.

In one embodiment, after the application of a luminescent material over the non-opaque surface, optical triangulation methods are used to determine the surface contour. The intra oral cavity is scanned by use of an intra oral apparatus, such as a mouthpiece. A scanning apparatus (Similar to that shown in FIGS. 1 and 4) contains the components to 1) illuminate the dental structure to be imaged; 2) digitally image a dental structure from different aspects; 3) reposition both the illumination and imaging apertures so as to traverse the entire intra oral cavity and to direct pressurized air at the dental structure that is being imaged to a) create a dry field; and b) allow sub gingival image capture; and 5) provides a spray orifice for dispensing a luminescent compound onto the dental structures during the digital imaging process. A luminescent substance such as phycobiliproteins/phycobilisomes, among others, is used as an imaging enhancing coating applied onto the dental structures during the digital imaging process.

One embodiment of the mouthpiece uses a single air jet and spray orifice (such as that shown in FIG. 2 above). At each lateral position, as the image aperture traverses an arc over the dental structure, a spray orifice is directed at the dental structure being imaged and dispenses the luminescent coating prior to image capture. The air jet output is then directed at the region of the dental structure just coated and dries the surface prior to the image capture. Yet another embodiment uses multiple air jets to simultaneously direct air at multiple regions of the dental structure in synchronism with the capture of the dental structure images (such as that shown in FIG. 3). In this embodiment a plurality of air jets are mounted in a known orientation to one another on a laterally moveable apparatus. The number of air jets and their orientation is selected to provide sufficient coverage and overlap of the dental structure to be digitally imaged and modeled. In this same embodiment (FIG. 3), multiple spray orifices are integrated into the mouthpiece to provide coverage of all areas that are being imaged. In either embodiment (FIG. 2 or FIG. 3), the pressurized air source may be integral to the mouthpiece or connected directly to the mouthpiece via tubing. In the latter case, the pressurized air source is ideally an existing source located at the patient dental chair. The mouthpiece would connect to this source using a standard industry interface.

As an alternative to spraying, the luminescent substance may be applied to the dental structures as a mouth rinse or as a brush-on or drench applied by the dentist just prior to imaging.

While the above embodiments have involved application of luminescent substances to dental structures, the invention is applicable to all non-opaque surfaces.

Although an illustrative embodiment of the present invention, and various modifications thereof, have been described in detail herein with reference to the accompanying drawings, it is to be understood that the invention is not limited to this precise embodiment and the described modifications, and that various changes and further modifications may be effected therein by one skilled in the art without departing from the scope or spirit of the invention as defined in the appended claims.

What is claimed is:

1. A method for generating a three-dimensional (3D) model of a structure, comprising:
    coating the structure with a luminescent substance to enhance the image quality, the luminescent substance having an excitation range;
    illuminating the structure with a structured light pattern;
    capturing one or more images of the structure through at least one image aperture each having a frequency sensitivity, wherein the frequency sensitivity of each image aperture is maximized for the luminescent material emission range.

2. The method of claim 1, further comprising illuminating the structure at a frequency within the excitation range of the luminescent material.

3. The method of claim 1, wherein the frequency sensitivity of each image aperture is attenuated for frequencies outside of the emission range of the luminescent material.

4. The method of claim 1, wherein the structure comprises tooth.

5. The method of claim 1, wherein the structure comprises a non-opaque structure.

6. The method of claim 1, wherein the structure comprises an opaque structure.

7. The method of claim 1, further comprising triangulating points on the images to determine a surface contour.

8. The method of claim 7, wherein the triangulating is optical triangulating.

9. The method of claim 1, wherein the structure is a tooth, further comprising applying the luminescent substance on the structure as a mouth rinse or as a brush-on or a drench prior to imaging.

10. The method of claim 1, further comprising spraying the structure with the luminescent substance using a nozzle.

11. A method for optically imaging a dental structure within an oral cavity, comprising:
   coating the structure with a luminescent substance to enhance the image quality, the luminescent substance having an excitation range;
   directing air at a tooth-gum interface of the dental structure through at least one air nozzle movably coupled to an intra-oral track;
   capturing one or more images of the dental structure through at least one image aperture with a multi-dimensional camera coupled to the image aperture, the image aperture movably coupled to an intra-oral track and having a frequency sensitivity, wherein the frequency sensitivity of the image aperture is maximized for the luminescent material emission range; and
   generating a three-dimensional (3D) model of the dental structure based on the images captured by the image aperture.

12. The method of claim 11, further comprising moving the air nozzle incrementally or continuously within the oral cavity.

13. The method of claim 12, further comprising actuating a motor to move the air nozzle incrementally or continuously within the oral cavity.

14. The method of claim 11, further comprising coating the dental structure with a substance to enhance the image quality.

15. The method of claim 11, further comprising providing an illuminator movably mounted on the intra-oral track to illuminate the dental structure.

16. The method of claim 15, further comprising moving the illuminator incrementally or continuously within the oral cavity.

17. The method of claim 1, wherein generating a three-dimensional model further comprises performing a stereometric analysis on the captured images.

18. The method of claim 1, wherein generating a three-dimensional model further comprises performing a scanning illumination beam and triangulation analysis on the captured images.

19. The method of claim 1, further comprising transmitting the 3D model over a network.

20. The method of claim 1, further comprising diagnosis and treatment of a patient using the 3D model.

21. A system to optically image a dental structure within an oral cavity, comprising:
   an intra-oral track adapted to be inserted inside the oral cavity;
   a spray orifice moveably coupled to the track to coat the dental structure with a luminescent material; and
   at least one image aperture movably coupled to the intra-oral track and adapted to capture one or more images of the dental structure.

22. A system to optically image a dental structure within an oral cavity, comprising:
   an intra-oral track adapted to be inserted inside the oral cavity;
   a pressurized air nozzle moveably coupled to the track to direct air at the dental structure;
   a spray orifice moveably coupled to the track to coat the dental structure with a luminescent material; and
   at least one image aperture movably coupled to the intra-oral track and adapted to capture one or more images of the dental structure.

* * * * *